(12) United States Patent
Mileham et al.

(10) Patent No.: US 6,850,405 B1
(45) Date of Patent: Feb. 1, 2005

(54) DUAL ANODE CAPACITOR INTERCONNECT DESIGN

(75) Inventors: Richard Mileham, Tonawanda, NY (US); Eric Stemen, Lancaster, NY (US); Laurie O'Connor, Williamsville, NY (US); William Elliott, Alden, NY (US); Joseph E. Spaulding, Williamsville, NY (US); Barry C. Muffoletto, Alden, NY (US); Douglas Eberhard, Grand Island, NY (US)

(73) Assignee: Wilson Greatbatch Technologies, Inc., Clarence, NY (US)

( * ) Notice: Subject to any disclaimer, the term of this patent is extended or adjusted under 35 U.S.C. 154(b) by 0 days.

(21) Appl. No.: 10/737,062

(22) Filed: Dec. 16, 2003

Related U.S. Application Data

(60) Provisional application No. 60/434,583, filed on Dec. 18, 2002, provisional application No. 60/433,680, filed on Dec. 16, 2002, and provisional application No. 60/433,681, filed on Dec. 16, 2002.

(51) Int. Cl.$^7$ .................................................. H01G 4/35
(52) U.S. Cl. ....................... 361/302; 361/361; 361/517; 361/535; 607/5; 29/25.41
(58) Field of Search .............................. 361/302, 301.3, 361/303, 508–509, 516, 517–518, 520, 528–529, 532, 535–538, 540; 29/25.41, 25.42; 607/5

(56) References Cited

U.S. PATENT DOCUMENTS

| | | | | |
|---|---|---|---|---|
| 5,894,403 A | * | 4/1999 | Shah et al. | 361/528 |
| 5,930,109 A | * | 7/1999 | Fishler | 361/508 |
| 6,191,931 B1 | * | 2/2001 | Paspa et al. | 361/302 |
| 6,224,985 B1 | * | 5/2001 | Shah et al. | 428/469 |

* cited by examiner

Primary Examiner—Anthony Dinkins
(74) Attorney, Agent, or Firm—Michael F. Scalise

(57) ABSTRACT

New designs that provide two anodes and their associated feedthroughs incorporated into one capacitor are described. The feedthrough wires can be in their own glass-to-metal seal or, they can be combined into one glass-to-metal seal as long as they are electrically insulated from each other. One embodiment has the anode feedthroughs left unconnected, while in other embodiments; they are joined externally of the capacitor casing. Several interconnect designs are described.

27 Claims, 9 Drawing Sheets

DUAL ANODE CAPACITOR INTERCONNECT DESIGN

CROSS-REFERENCE TO RELATED APPLICATIONS

The present application claims priority based upon provisional application Ser. No. 60/433,680, filed Dec. 16, 2002; 60/433,681, filed Dec. 16, 2002; and 60/434,583, filed Dec. 18, 2002.

BACKGROUND OF THE INVENTION

The present invention generally relates to a capacitor and, more particularly, to a capacitor containing two anodes having their respective feedthroughs connected to a common terminal external of the casing.

SUMMARY OF THE INVENTION

As more and more medical applications are investigated and implemented to aid and assist the human body, devices needed to deliver the desired therapy are becoming increasingly more sophisticated, both functionally and in terms of their structural makeup. Modern implantable devices require power sources that are smaller in size, but powerful enough to meet the therapy requirements. For example, a cardiac defibrillator has a battery powering circuits performing such functions as, for example, the heart sensing and pacing functions. This requires electrical current of about 1 microampere to about 100 milliamperes. From time-to-time, the cardiac defibrillator may require a generally high rate, pulse discharge load component that occurs, for example, during charging of a capacitor assembly in the defibrillator for the purpose of delivering an electrical shock to the heart to treat tachyarrhythmias, the irregular, rapid heartbeats that can be fatal if left uncorrected. This requires electrical current of about 1 ampere to about 4 amperes.

The current trend in medicine is to make cardiac defibrillators, and like implantable devices, as small and lightweight as possible without compromising their power. This, in turn, means that capacitors contained in these devices must be readily adaptable in how they are connected to each other as well as to the battery and the device circuitry. In that light, the present invention relates to a new design that provides two anodes and their associated feedthroughs incorporated into one capacitor. The feedthrough wires can be in their own glass-to-metal seal or, they can be combined into one glass-to-metal seal as long as they are electrically insulated from each other. One embodiment has the anode feedthroughs left unconnected, while in other embodiments; they are joined externally of the capacitor casing. Several interconnect designs are described.

These and other aspects of the present invention will become more apparent to those skilled in the art by reference to the following description and to the appended drawings.

BRIEF DESCRIPTION OF THE DRAWINGS

FIG. 2A is a cross-sectional view along line 2A—2A of FIG. 2.

FIG. 2B is a side elevational view of a cathode current collector 34 before it is incorporated into the capacitor 10 illustrated in FIG. 1.

DETAILED DESCRIPTION OF THE PREFERRED EMBODIMENTS

Figure 1:
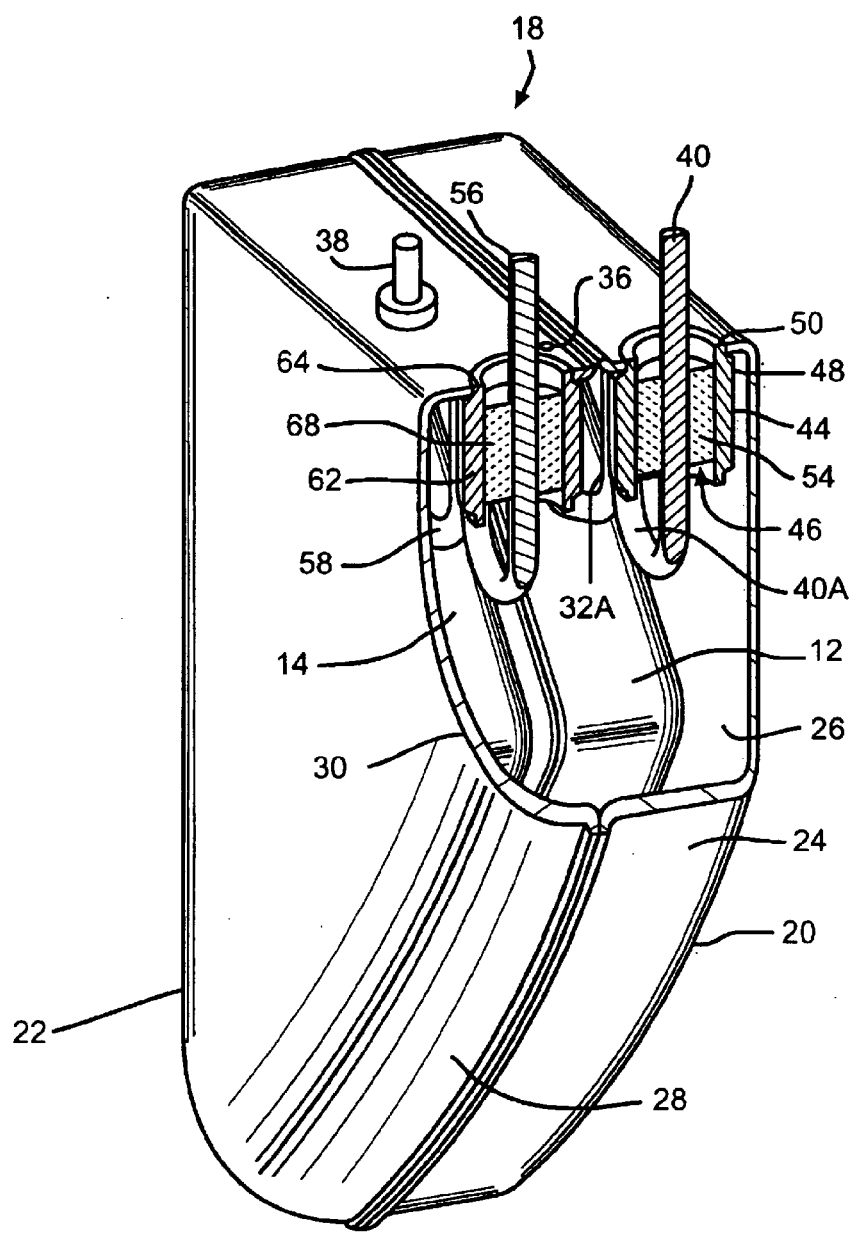
FIG. 1 is a perspective view looking at the left edge of a dual anode capacitor 10 according to the present invention with the anode feedthroughs 40, 56 left unconnected.
Figure 4:
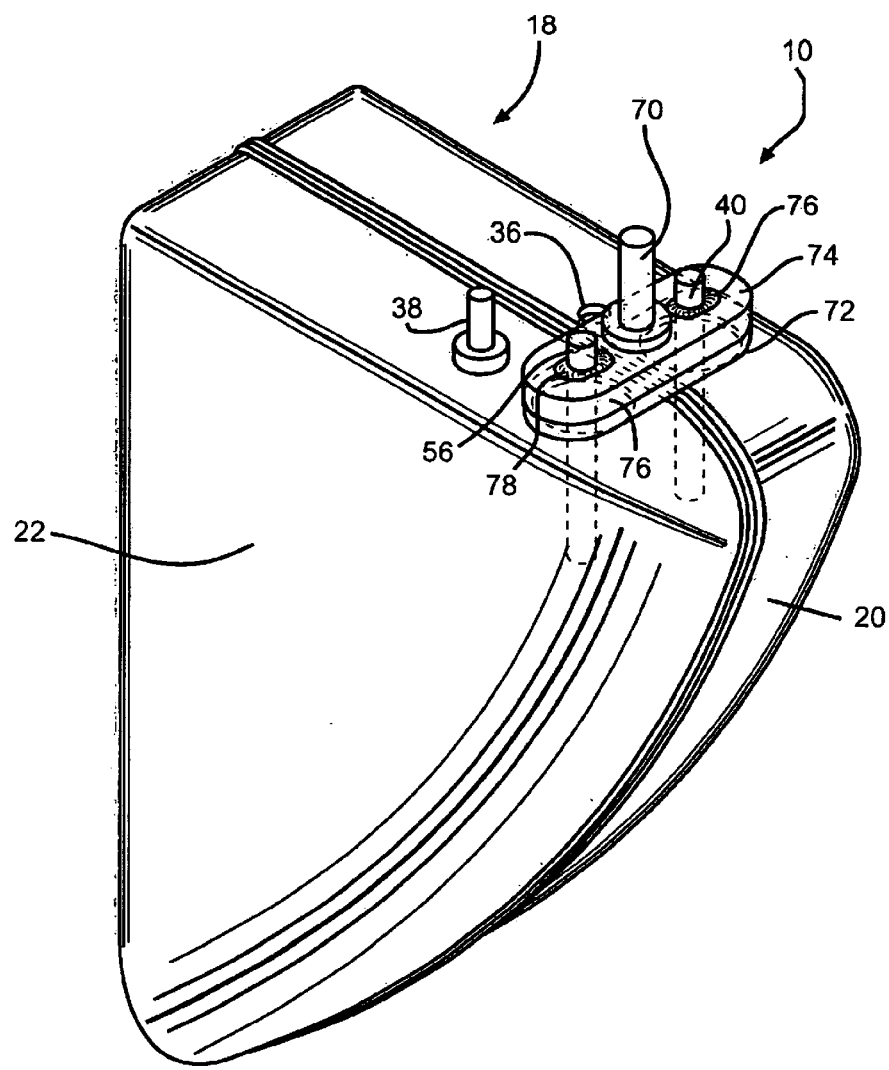
FIG. 4 is a perspective view of the capacitor of FIG. 1 with the anode feedthroughs 40, 56 joined externally of the casing.

Referring now to the drawings, FIGS. 1 and 4 to 9 are perspective views showing various embodiments of capacitors according to the present invention. It should be pointed out that the capacitor 10 illustrated in FIGS. 1 and 4 are identical except for the external connection for joining the anode feedthroughs together. The capacitor 10 in FIG. 1 has the anode feedthroughs left unconnected while in FIG. 4 they are joined to each other externally of the casing.

Figure 2:
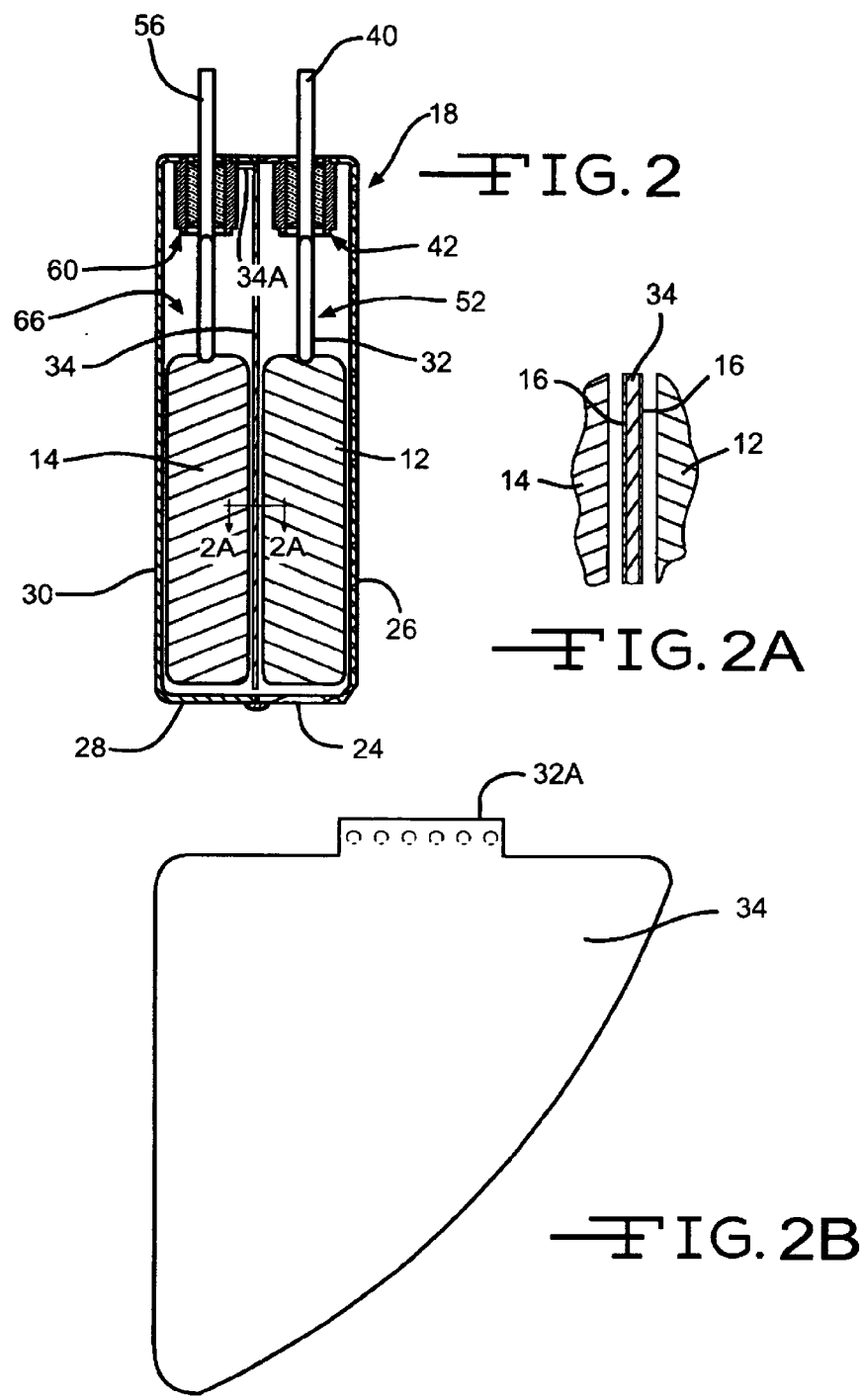
FIG. 2 is a cross-sectional view of the capacitor 10 illustrated in FIG. 1.
Figure 3:
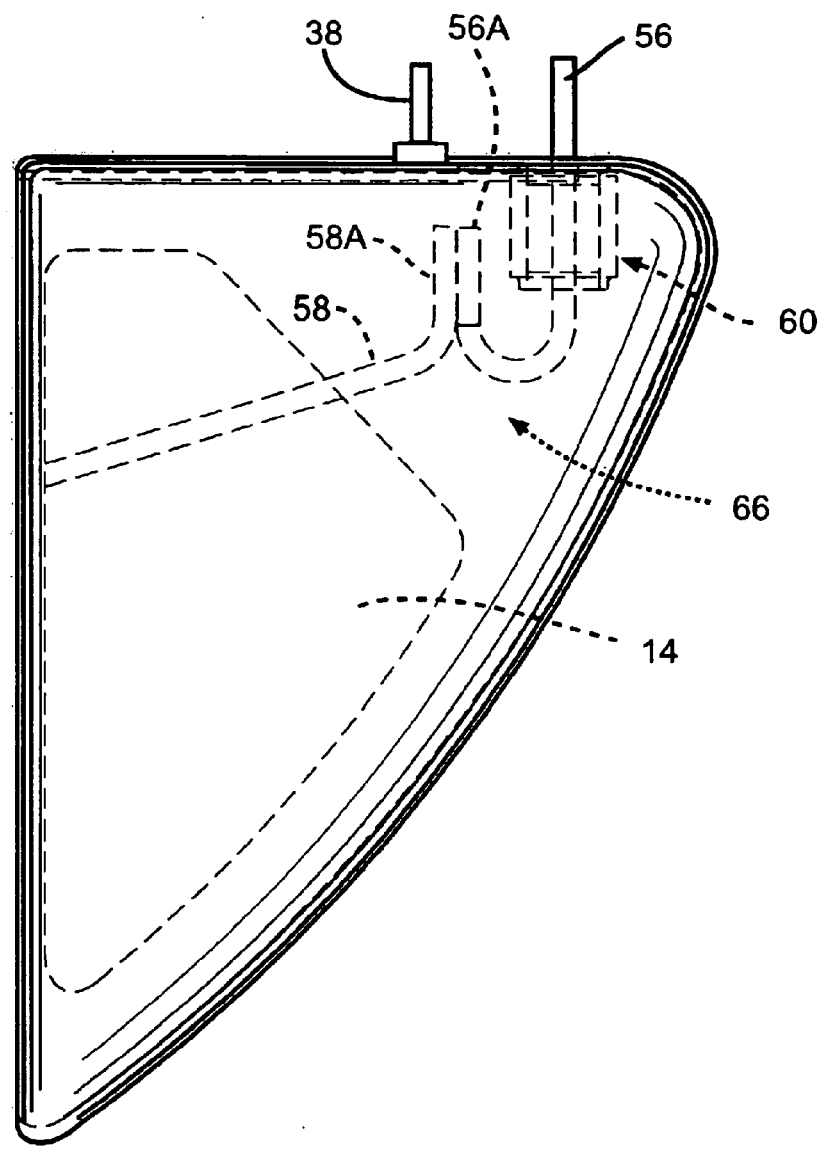
FIG. 3 is a side elevational view, partly in phantom, of the dual anode capacitor 10 of FIG. 1.

As shown in FIGS. 1 to 3, a first embodiment of the capacitor 10 comprises a first anode 12 of a first anode active material, a second anode 14 of a second anode active material and a cathode of a cathode active material 16 housed inside a hermetically sealed casing 18. The capacitor electrodes are operatively associated with each other by an electrolyte (not shown) contained inside the casing, as will be described in detail hereinafter. The capacitor 10 can be of either an electrochemical type wherein the anode and the cathode electrodes are provided by conductive substrates having a capacitive material contacted thereto or, an electrolyte type wherein the cathode electrode is provided by a conductive substrate having capacitive properties. The illustrated capacitors are preferably of the latter type, however, that should not be construed as limiting.

As particularly shown in FIGS. 1 and 2, casing 18 is of a metal material comprising first and second casing portions 20 and 22. Casing portion 20 comprises a surrounding sidewall 24 extending to a face wall 26. Similarly, casing portion 22 comprises a surrounding sidewall 28 extending to a face wall 30. The sidewalls 24 and 28 are sized to butt up to each other. Then, the casing portions 20, 22 are hermetically sealed together by welding the sidewalls 24, 28 where they contact. The weld is provided by any conventional means; however, a preferred method is by laser welding.

The anode active material of the anodes 12 and 14 is typically of a metal selected from the group consisting of tantalum, aluminum, titanium, niobium, zirconium, hafnium, tungsten, molybdenum, vanadium, silicon, germanium, and mixtures thereof in the form of a pellet. As is well known by those skilled in the art, the anode metal in powdered form, for example tantalum powder, is compressed into a pellet having an anode wire 32 (FIG. 1) embedded therein and extending there from, and sintered under a vacuum at high temperatures. The porous body is then anodized in a suitable electrolyte to fill its pores with the electrolyte and to form a continuous dielectric oxide film on the sintered body. The assembly is then formed to a desired voltage to produce an oxide layer over the sintered body and anode wire. The anode can also be of an etched aluminum or titanium foil.

Portions of the cathode active material contact the inner surfaces of the casing face walls 26, 30. Another portion of the cathode active material 16 is positioned intermediate the anodes 12, 14. The cathode active material 16 intermediate the anode is supported on the opposed inner surfaces of a current collector 34 (FIG. 2B), preferably in the form of a foil. A tab 34A provides for tack welding the current collector 34 to the inner surface of the surrounding sidewall 28 of casing portion 22. The current collector 34 is then bent relative to the tab 34A to position it intermediate the anodes 12, 14.

The cathode active material has a thickness of about a few hundred Angstroms to about 0.1 millimeters directly coated on the inner surface of the face walls 26, 30 or, it is coated on a conductive substrate (not shown) in electrical contact with the inner surface of the face walls. In that respect, the face walls 26, 30 and the current collector 34 may be of an anodized-etched conductive material, have a sintered active material with or without oxide contacted thereto, be contacted with a double layer capacitive material, for example a finely divided carbonaceous material such as graphite or carbon or platinum black, a redox, pseudocapacitive or an under potential material, or be an electroactive conducting polymer such as polyaniline, polypyrole, polythiophene, and polyacetylene, and mixtures thereof.

According to one preferred aspect of the present invention, the redox or cathode active material 16 includes an oxide of a first metal, the nitride of the first metal, the carbon nitride of the first metal, and/or the carbide of the first metal, the oxide, nitride, carbon nitride and carbide having pseudocapacitive properties. The first metal is preferably selected from the group consisting of ruthenium, cobalt, manganese, molybdenum, tungsten, tantalum, iron, niobium, iridium, titanium, zirconium, hafnium, rhodium, vanadium, osmium, palladium, platinum, nickel, and lead.

The cathode active material 16 may also include a second or more metals. The second metal is in the form of an oxide, a nitride, a carbon nitride or carbide, and is not essential to the intended use of the conductive face walls 26, 30 and the intermediate current collector 34 as a capacitor electrode, and the like. The second metal is different than the first metal and is selected from one or more of the group consisting of tantalum, titanium, nickel, iridium, platinum, palladium, gold, silver, cobalt, molybdenum, ruthenium, manganese, tungsten, iron, zirconium, hafnium, rhodium, vanadium, osmium, and niobium. In a preferred embodiment of the invention, the cathode active material 16 includes an oxide of ruthenium or oxides of ruthenium and tantalum.

The mating casing portions 20, 22, and the electrically connected conductive substrate if it is provided, are preferably selected from the group consisting of tantalum, titanium, nickel, molybdenum, niobium, cobalt, stainless steel, tungsten, platinum, palladium, gold, silver, copper, chromium, vanadium, aluminum, zirconium, hafnium, zinc, iron, and mixtures and alloys thereof. Preferably, the face and sidewalls of the casing portions and the current collector 34 have a thickness of about 0.001 to about 2 millimeters.

The exemplary electrolytic type capacitor shown in FIGS. 1 to 3 has the cathode active material 16 preferably coating the face walls 26, 30 spaced from the respective sidewalls 24, 28. Such a coating is accomplished by providing the conductive face walls 26, 30 with a masking material in a known manner so that only an intended area of the face walls is contacted with active material. The masking material is removed from the face walls prior to capacitor fabrication. Preferably, the cathode active material 16 is substantially aligned in a face-to-face relationship with the major faces of the anodes 12, 14.

A preferred coating process is in the form of an ultrasonically generated aerosol as described in U.S. Pat. Nos. 5,894,403; 5,920,455; 6,224,985; and 6,468,605, all to Shah et al. These patents are assigned to the assignee of the present invention and incorporated herein by reference. In that manner, the ultrasonically generated active material contacted to the conductive surfaces has a majority of its particles with diameters of less than about 10 microns. This provides an internal surface area for the active material of about 10 $m^2$/gram to about 1,500 $m^2$/gram.

A separator (not shown) of electrically insulative material is provided between the anodes 12 and 14 and the cathode active materials 16 to prevent an internal electrical short circuit between them. The separator material also is chemically unreactive with the anode and cathode active materials and both chemically unreactive with and insoluble in the electrolyte. In addition, the separator material has a degree of porosity sufficient to allow flow there through of the electrolyte during the electrochemical reaction of the capacitor 10. Illustrative separator materials include woven and non-woven fabrics of polyolefinic fibers including polypropylene and polyethylene or fluoropolymeric fibers including polyvinylidene fluoride, polyethylenetetrafluoroethylene, and polyethylenechlorotrifluoroethylene laminated or superposed with a polyolefinic or fluoropolymeric microporous film, non-woven glass, glass fiber materials and ceramic materials. Suitable microporous films include a polyethylene membrane commercially available under the designation SOLUPOR® (DMS Solutech), a polytetrafluoroethylene membrane commercially available under the designation ZITEX® (Chemplast Inc.), a polypropylene membrane commercially available under the designation CELGARD® (Celanese Plastic Company, Inc.), and a membrane commercially available under the designation DEXIGLAS® (C. H. Dexter, Div., Dexter Corp.). Cellulose based separators also typically used in capacitors are contemplated by the scope of the present invention. Depending on the electrolyte used, the separator can be treated to improve its wettability, as is well known by those skilled in the art.

A suitable electrolyte for the capacitor 10 is described in U.S. Pat. No. 6,219,222 to Shah et al., which includes a mixed solvent of water and ethylene glycol having an ammonium salt dissolved therein. U.S. Pub. Nos. 20030090857 and 20030142464 describe other electrolytes for the present capacitors. The electrolyte of the former publication comprises water, a water-soluble inorganic and/or organic acid and/or salt, and a water-soluble nitroaromatic compound while the latter relates to an electrolyte having de-ionized water, an organic solvent, isobutyric acid and a concentrated ammonium salt. These publications and patent are assigned to the assignee of the present invention and incorporated herein by reference. The electrolyte is provided inside the hermetically sealed casing through a fill opening closed by a hermetic closure 36, as is well known by those skilled in the art.

The casing 18, including the portions 20, 22, being of a conductive metal serves as one terminal for making electrical connection between the capacitor 10 and its load. A pin 38 is welded to the sidewall 24 to provide the negative terminal for the capacitor 10.

As shown in FIGS. 1 and 2, a conductor or feedthrough lead 40 connected to the anode wire 32 extends from the anode 12 housed in the casing 18 and through the first surrounding sidewall 24. The anode feedthrough 40 is electrically insulated from the metal casing 18 by an insulator glass-to-metal seal 42. The glass-to-metal seal comprises a ferrule 44 defining an internal cylindrical through bore or passage 46 of constant inside diameter. An annular step 48 provided at the upper end is of an outer diameter sized to fit in a closely spaced relationship in an annular opening 50 in the first casing sidewall 24 with the remaining body of the ferrule butted against the inner surface of the sidewall. The ferrule 44 is secured therein by welding, and the like.

As shown in FIGS. 2 and 3, the anode 12 has a notch 52 that provides clearance for the glass-to-metal seal 42. The anode wire 32 embedded in the anode active material extends outwardly from the notch 52 and has a distal end 32A bent into a position generally parallel to the longitudinal axis of ferrule 44. A proximal end 40A of the anode feedthrough 40 is bent into a J-hook shape to align parallel with the distal end 32A of the anode wire 32. The distal end 32A of the anode wire is then welded to the proximal end 40A of the anode feedthrough to electrically connect the anode to the feedthrough 40.

An insulative glass 54 provides a hermetic seal between the inside of the ferrule 44 and the anode feedthrough 40. The glass is, for example, ELAN® type 88 or MANSOL™ type 88. The anode feedthrough 40 preferably comprises the same material as the anode active material. In that manner, the portion of the anode feedthrough 40 extending outside the capacitor 10 is hermetically sealed from the interior of the capacitor and insulated from the mating casing portions 20, 22 serving as the terminal for the cathode electrode.

The other anode 14 likewise has a conductor or feedthrough lead 56 connected to an anode wire 58 that extends from the anode and through the second surrounding side wall 28. The anode feedthrough 56 is electrically insulated from the metal casing 18 by a glass-to-metal seal 60 comprising a cylindrically shaped ferrule 62. An upper step of the ferrule 62 fits in a closely spaced relationship in an annular opening 64 in the second casing sidewall 28 with the ferrule butted against the inner surface of the sidewall. The ferrule 62 is secured therein by welding, and the like.

In a similar manner as anode 12, anode 14 has a notch 66 (FIGS. 2 and 3) that provides clearance for the glass-to-metal seal 60. The anode wire 58 embedded in the anode active material extends outwardly from the notch with a distal end 58A bent into a position generally parallel to the longitudinal axis of the ferrule 62. A proximal end 56A of the anode feedthrough 56 is bent into a J-hook shape to align parallel with the distal end 58A of the anode wire 58. Welding then electrically connects the anode wire 58 to the feedthrough 56.

An insulative glass 68, similar to glass 54 of the glass-to-metal seal 42 for the anode 12, seals between the inside of the ferrule 62 and the anode feedthrough 56. This glass hermetically seals that portion of the anode feedthrough 56 extending outside the capacitor 10 from the capacitor interior, insulated from the mating casing portions 20, 22.

The capacitor 10 illustrated in FIGS. 1 to 3 has the anode feedthroughs 40, 56 left unconnected to each other. This means that the respective anodes 12, 14 are capable of being charged independently of each other. This could take the form of charging one of the anodes partially or completely to a rated voltage, and then charging the other anode. In other situations, it might be preferred to charge one of the anodes at a rate different than that at which the second anode is charged. For example, a pulse current could charge one of the anodes while the other is by constant power charging. An advantage of separately connecting the anode feedthroughs 40, 56 to an external charging circuit is that the charging or discharging currents can be distributed over the several feedthroughs, which allows smaller, more flexible leads and connections than one lead with an equivalent current carrying capacity.

As shown in FIG. 4, the anode feedthroughs 40 and 56 for the respective anodes 12, 14 are electrically connected to a common positive polarity terminal 70. This is accomplished by first mounting an insulator 72 having spaced apart openings sized to receive the feedthroughs 40, 56 when resting on the casing portion sidewalls 24, 28. A bridge 74 of a conductive material, for example, nickel, is then supported on the insulator 72. The bridge has a pair of openings that surround the anode feedthroughs 40, 56. The bridge 74 is secured to the feedthroughs 40, 56 by respective welds 76 and 78 to electrically connect them together. Finally, the common positive terminal 70 is electrically connected to bridge 74. The terminal 70 has an enlarged base that is positioned about at the midpoint on the bridge between the feedthroughs 40, 56. In that manner, the terminal 70 is aligned along a common axis with the feedthroughs 40, 56 and electrically secured thereto, such as by welding or soldering. The bridge can also be crimped onto the feedthroughs 40, 56 by applying a force that deforms the bridge from opposed directions onto the feedthroughs.

The capacitor 10 is then connectable to a load (not shown) as a power source. Connecting the negative polarity terminal pin 38 and the common positive terminal 82 does this.

Figure 5:
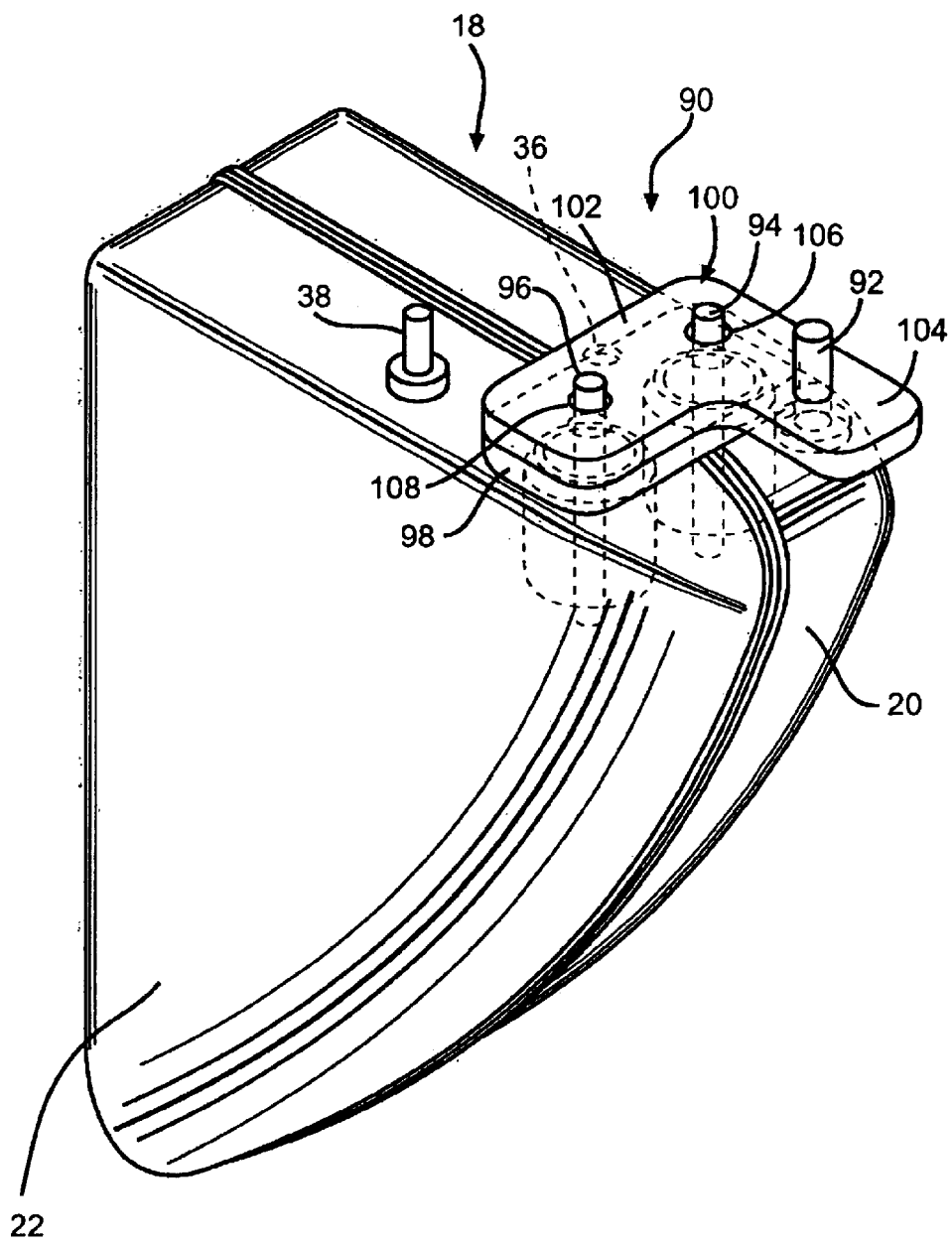
FIGS. 5 to 8 are perspective views looking at the left edge of various embodiments of dual anode capacitors 90, 110, 130 and 150 according to the present invention.

FIG. 5 shows a capacitor 90 having another embodiment of a structure for providing a common positive terminal 92 accordingly to the present invention. The capacitor 90 includes all of the aspects of the previously described capacitor 10. However, in this capacitor 90 the anode feedthroughs 94, 96 are provided with an insulator 98 having spaced apart openings sized to receive the feedthroughs. An L-shaped bridge 100 of a conductive material is provided having a base portion 102 and an extending portion 104. The base portion 102 has spaced apart openings sized to receive the feedthroughs 94, 96 with the bridge 100 resting on the casing portion sidewalls 24, 28. Welds 106 and 108 are then provided to electrically connect the bridge 100 to the feedthroughs 94, 96. Finally, the positive terminal 92 is electrically connected to the extending portion 104 of the bridge 100. Alternatively, the positive terminal 92 and the bridge 100 are a unitary member. The capacitor is then connected to a load (not shown) through the negative polarity terminal pin 38 and the positive terminal 92.

Figure 6:
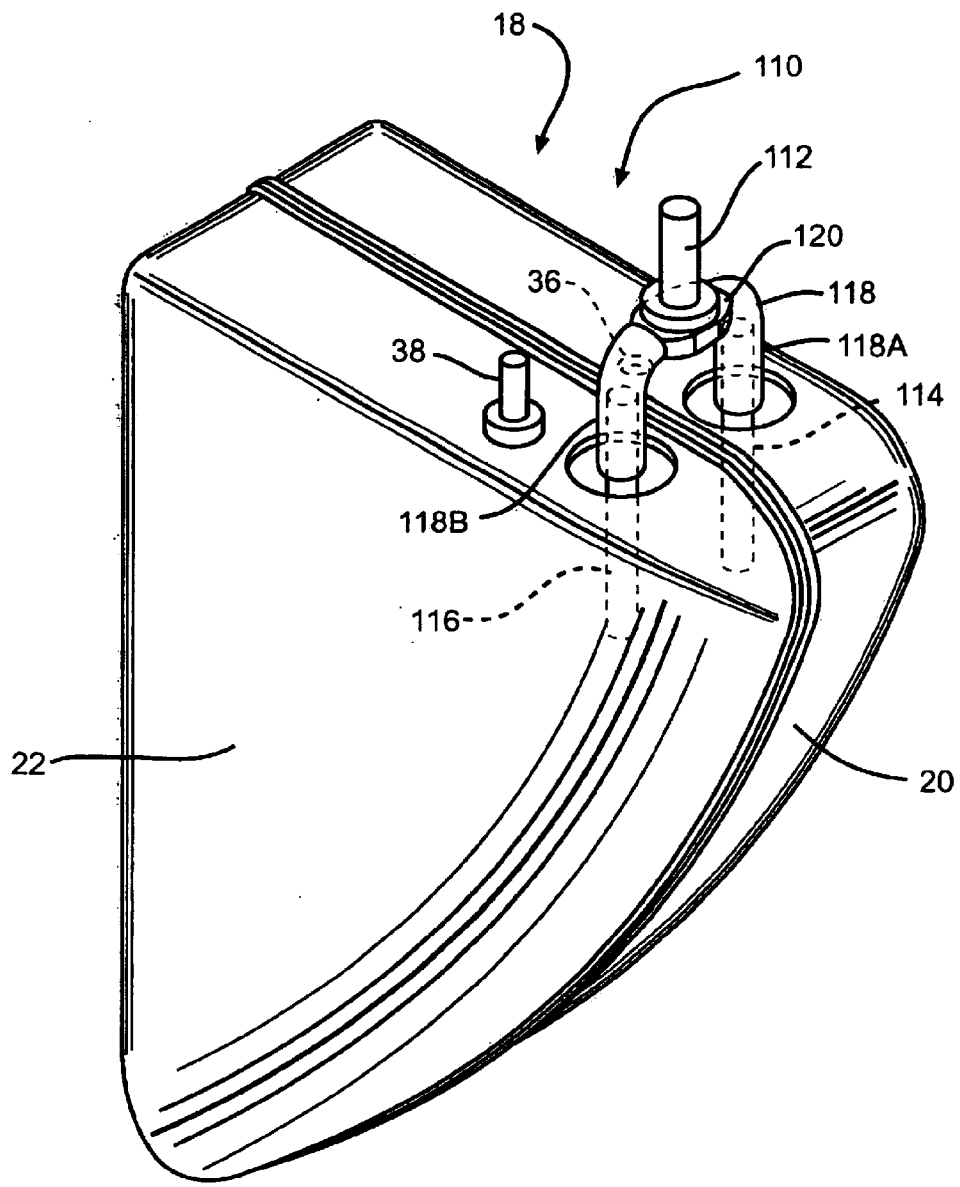

FIG. 6 shows a capacitor 110 comprising another embodiment of a structure for providing a common positive terminal 112 according to the present invention. The capacitor 110 includes all of the aspects of the previously described capacitor 10 except that the anode feedthroughs 114, 116 are electrically connected together by an inverted U-shaped union 118. The union 118 has bores provided in its legs 118A and 118B that mate with the anode feedthroughs 114, 116, respectively. Crimping the legs down onto the feedthroughs then makes a secure electrochemical connection. Alternatively, welding, soldering, and the like make this connection.

The union 118 comprises a land 120 intermediate the legs 118A, 118B. The land provides a relatively planar surface for supporting the positive terminal 112. Alternatively, the positive terminal 112 and the union 118 including the land 120 are a unitary member.

Figure 7:
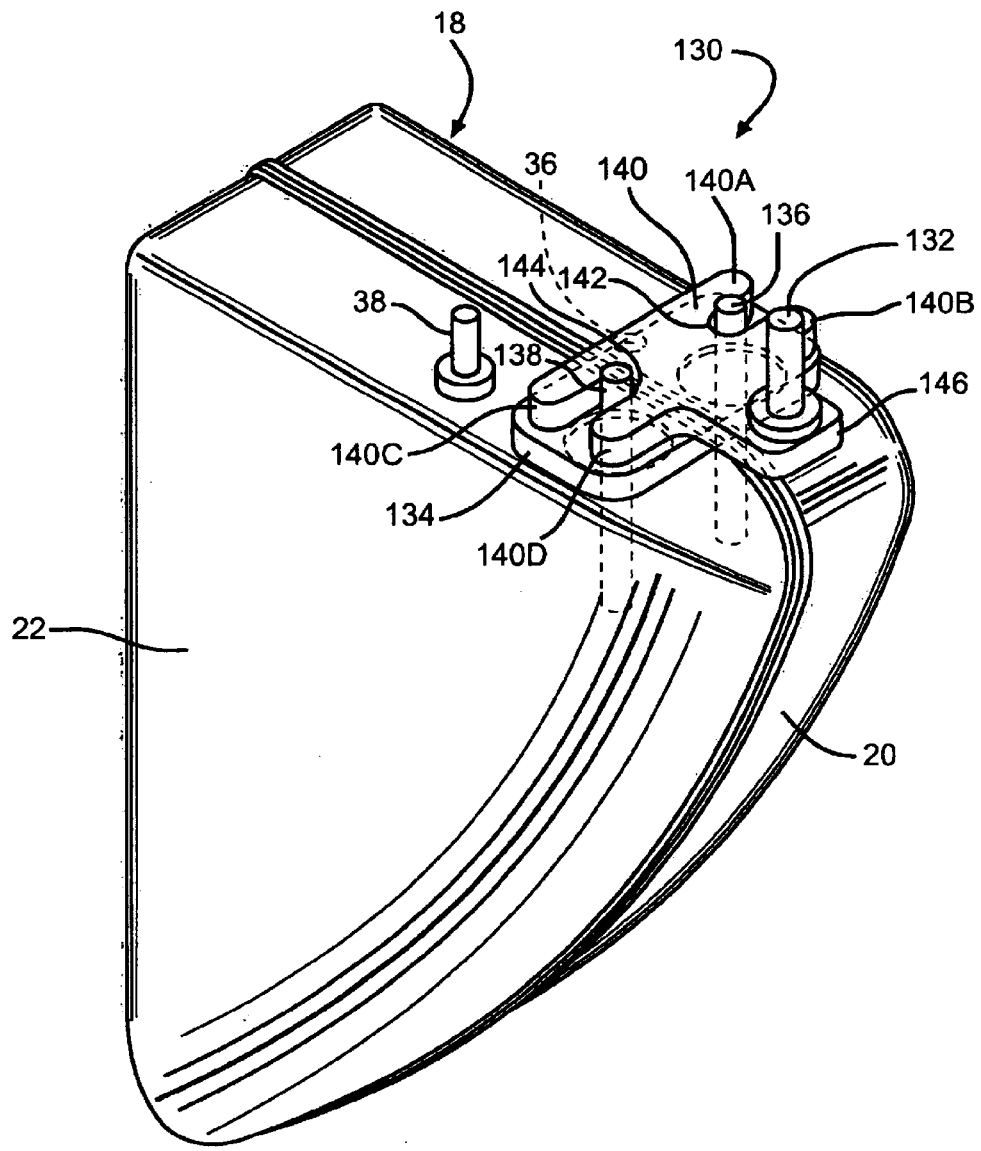

FIG. 7 illustrates a capacitor 130 comprising another embodiment of a structure for providing a common positive terminal 132 according to the present invention. The capacitor 130 includes all of the aspects of the previously described capacitor 10. However, a generally rectangular shaped insulator 134 is provided with spaced apart openings sized to receive the anode feedthroughs 136, 138. A conductive bridge 140 has a somewhat rectangular shape matching that of the insulator 134. The bridge 140 is provided with opposed inlets 142 and 144. The terminus of each inlet is positioned such that with the bridge 140 supported on the insulator 134, the anode feedthroughs 136, 138 are in a closely spaced relationship with the bridge there. That way, inlet 142 provides spaced apart ears 140A and 140B that are crimped or otherwise deformed to capture the anode feedthrough 146 electrically connected to the bridge 140. Similarly, inlet 144 provides spaced apart ears 140C and 140D that are crimped or otherwise deformed to capture the anode feedthrough 138 electrically connected to the bridge. A protrusion 146 extends outwardly from the front wall of the bridge 140 and supports the positive terminal 132 secured thereto, such as by welding, and the like.

Figure 8:
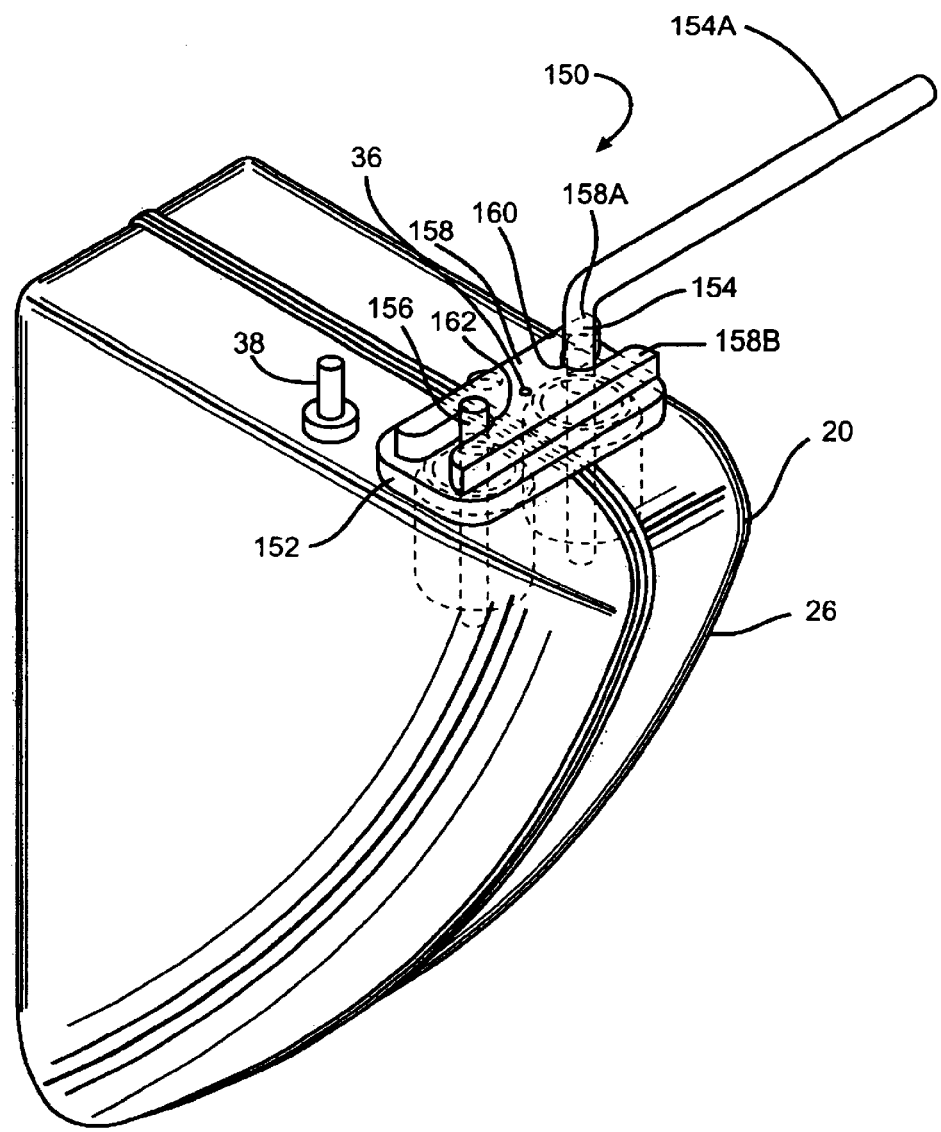

FIG. 8 illustrates a dual anode capacitor 150 comprising another embodiment for providing a common positive terminal according to the present invention. The capacitor 150 includes all of the aspects of the previously described capacitor 10. However, a generally rectangular shaped insulator 152 is provided with spaced apart openings that receive the anode feedthroughs 154 and 156 with the insulator supported on the casing. A conductive bridge 158 has a somewhat rectangular shape matching that of the insulator 152. The bridge 158 is provided with inlets 160 and 162 such that when the bridge is supported on the insulator 152, the anode feedthroughs 154, 156 are in a closely spaced relationship with a terminus of the inlets. This provides spaced apart ears 158A and 158B that are crimped or otherwise deformed to capture the anode feedthrough 154 electrically connected to the bridge. Similarly, inlet 162 provides spaced apart ears 158C and 158D that are crimped or otherwise deformed to capture the anode feedthrough 156 electrically connected to the bridge.

One of the anode feedthroughs, in the illustrated capacitor it is anode feedthrough 154, comprises an extension portion 154A positioned at a perpendicular orientation with respect to the longitudinally axis of the feedthrough. The extension 154A is substantially greater in length than the other feedthrough 156 and extends outwardly past the face wall 26 of casing portion 20, and oriented generally normal to the plane formed thereby. That way, the extension 146A provides a bar structure for connecting to a load anywhere along its length.

Figure 9:
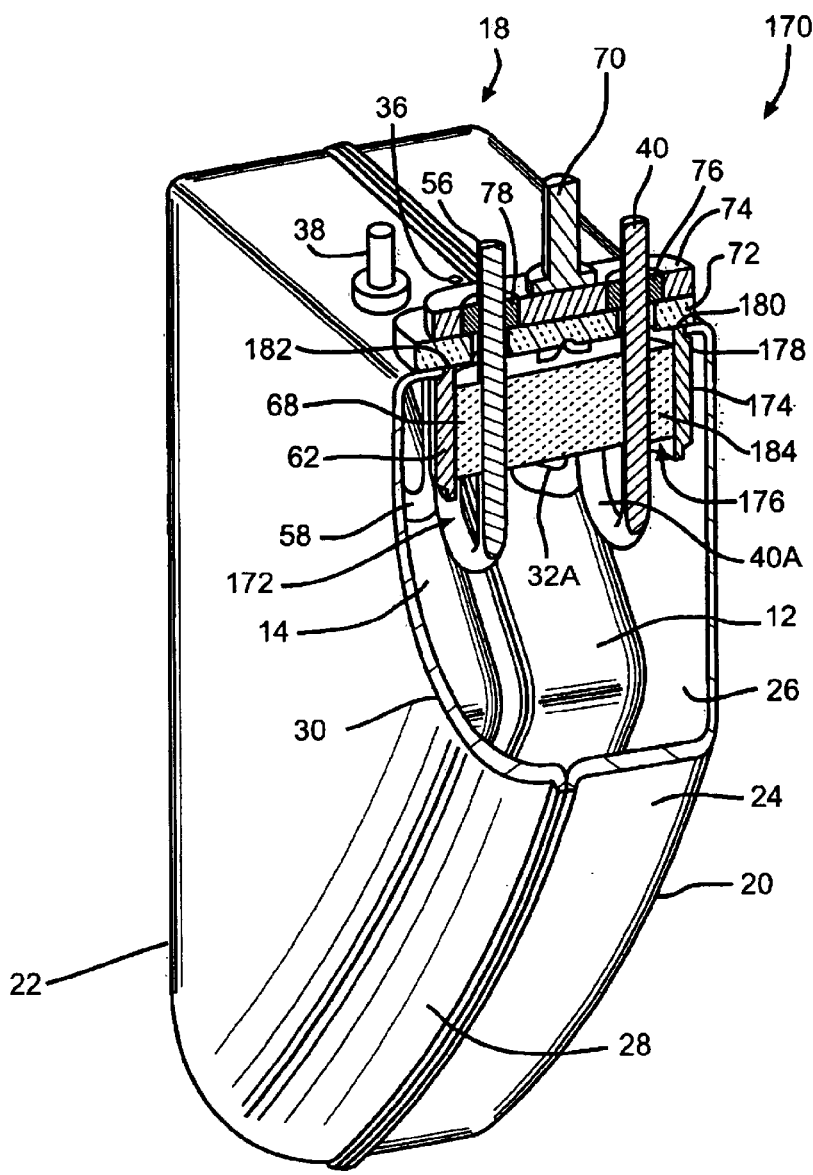
FIG. 9 is a side elevational view of the capacitor 10 of FIG. 1 with the anode feedthroughs 40, 56 electrically isolated from the casing 18, but extending through a single ferrule.

FIG. 9 illustrates a capacitor 170 that is similar to capacitor 10 shown n FIGS. 1 to 4. However capacitor 170 has the anode feedthroughs 40, 56 electrically isolated from each other and from the casing 18 by a unitary glass-to-metal seal 172. The glass-to-metal seal comprises a ferrule 174 defining an internal oblong-shaped through bore or passage 176. A surrounding step 178 provided at the upper end is sized to fit in a closely spaced relationship in an inlet 180 in the sidewall 24 of the first casing portion 20. The second casing portion 22 has a matching inlet 182. The first casing portion is then mated to the second portion with the sidewalls 24, 28 contacting each other at their outer edges. This serves to capture the ferrule 174 between the casing portions when they are secured to each other and to the ferrule step 178, such as by welding, soldering and the like. An insulative glass 184 is provided between the inside of the ferrule 174 and the anode feedthroughs 40, 56.

In all other respects, capacitor 170 is the same as capacitor 10 shown in FIG. 4. This includes the anode feedthroughs 40, 56 being electrically connected to a common positive polarity terminal 70. The terminal is supported by a bridge 74 having openings receiving the feedthroughs 40, 56. The bridge is insulated from the casing 18 by an insulator 72 and electrically connected to the feedthroughs by respective welds or solders 76, 78. The bridge can also be deformed into electrical contact with the feedthroughs.

Thus, it is apparent that the present invention directed to a multiple anode, multiple feedthrough capacitor, such as a wet tantalum capacitor, has many advantages over the current practice of incorporating multiple capacitors in a device with one anode and one feedthrough per capacitor. These include a lower ESR allowed by multiple anodes while avoiding a decrease in energy density required by the internal connection of the anodes to one feedthrough, ease of attaching the anode wires to one feedthrough, and ease of assembly.

It is appreciated that various modifications to the inventive concepts described herein may be apparent to those of ordinary skill in the art without departing from the spirit and scope of the present invention as defined by the appended claims.

What is claimed is:

1. A capacitor, which comprises:
   a) a casing;
   b) a first anode electrically connected to a first feedthrough extending outside the casing, wherein the first feedthrough is insulated from the casing;
   c) a second anode electrically connected to a second feedthrough extending outside the casing, wherein the second feedthrough is insulated from the casing and wherein the first and second anodes are connected to a common terminal external of the casing;
   d) a cathode of a cathode active material facing at least a portion of each of the first and second anodes; and
   e) an electrolyte operatively associating the cathode active material with the first and second anodes housed inside the casing.

2. The capacitor of claim 1 wherein the casing is the terminal for the cathode.

3. The capacitor of claim 1 wherein the feedthroughs for the first and second anodes are isolated from the casing by respective glass-to-metal seals.

4. The capacitor of claim 1 wherein the feedthroughs for the first and second anodes are spaced apart from each other but isolated from the casing by a single glass-to-metal seal.

5. The capacitor of claim 1 including a bridge having first and second openings that receive the first and second feedthroughs when the bridge is supported on the casing and electrically isolated therefrom.

6. The capacitor of claim 5 wherein the bridge is secured to the first and second feedthroughs by a solder or weld material in the first and second openings.

7. The capacitor of claim 5 wherein the bridge is deformed into contact with the first and second feedthroughs.

8. The capacitor of claim 5 wherein the bridge supports an anode terminal intermediate the first and second feedthroughs.

9. The capacitor of claim 5 wherein the bridge comprises an extension that supports an anode terminal.

10. The capacitor of claim 5 wherein the bridge is an inverted U-shaped member having spaced apart first and second legs that mate with the first and second feedthroughs, respectively.

11. The capacitor of claim 5 wherein the bridge comprises first and second pairs of ears deformable into contact with the first and second feedthroughs, respectively.

12. The capacitor of claim 5 wherein at least one of the first and second feedthroughs comprises an extension portion that is substantially greater in length than the other feedthrough to provide a bar for connection to a load.

13. The capacitor of claim 1 wherein the casing comprises first and second portions, the first portion having a first face wall extending to a surrounding first sidewall and the second portion having a second face wall extending to a surrounding second sidewall, and wherein the first and second sidewalls are secured together to provide the casing.

14. The capacitor of claim 13 wherein the first and second face walls support the cathode active material opposite the respective first and second anodes.

15. The capacitor of claim 13 wherein a current collector is disposed intermediate the first and second anodes, the current collector having opposed first and second major faces provided with cathode active material and positioned opposite the first and second anodes.

16. The capacitor of claim 1 wherein the first and second anodes comprise tantalum and the cathode active material comprises ruthenium.

17. A method for providing a capacitor, comprising the steps of:
 a) providing a casing comprising a first casing portion and a second casing portion;
 b) positioning a first anode inside the first casing portion, the first anode having a first feedthrough electrically connected thereto and extending outside the first casing portion and including insulating the first feedthrough from the first casing portion;
 c) positioning a second anode inside the second casing portion, the second anode having a second feedthrough electrically connected thereto and extending outside the second casing portion and including insulating the second feedthrough from the second casing portion;
 d) positioning a cathode of a cathode active material inside at least one of the first and second casing portions;
 e) securing the first casing portion to the second casing portion to provide an enclosure containing the first and second anodes and the cathode; and
 f) providing an electrolyte inside the casing to operatively associate the cathode with the first and second anodes.

18. The method of claim 17 including beginning charging the first anode followed by beginning charging the second anode after charging the first anode has already begun.

19. The method of claim 17 including charging the first and second anodes independent of each other.

20. The method of claim 17 including connecting the first and second anodes to a common terminal external of the casing, and then charging them simultaneously.

21. A capacitor, which comprises:
 a) a casing;
 b) a first anode electrically connected to a first feedthrough extending outside the casing, wherein the first feedthrough is insulated from the casing;
 c) a second anode electrically connected to a second feedthrough extending outside the casing, wherein the second feedthrough is insulated from the casing;
 d) a cathode of a cathode active material facing at least a portion of each of the first and second anodes, wherein the casing is the terminal for the cathode; and
 e) an electrolyte operatively associating the cathode active material with the first and second anodes housed inside the casing.

22. The capacitor of claim 21 wherein the first and second anodes are connected to a common terminal external of the casing.

23. A capacitor, which comprises:
 a) a casing;
 b) a first anode electrically connected to a first feedthrough extending outside the casing, wherein the first feedthrough is insulated from the casing;
 c) a second anode electrically connected to a second feedthrough extending outside the casing, wherein the second feedthrough is insulated from the casing and wherein the feedthroughs for the first and second anodes are isolated from the casing by respective glass-to-metal seals;
 d) a cathode of a cathode active material facing at least a portion of each of the first and second anodes; and
 e) an electrolyte operatively associating the cathode active material with the first and second anodes housed inside the casing.

24. A capacitor, which comprises:
 a) a casing;
 b) a first anode electrically connected to a first feedthrough extending outside the casing, wherein the first feedthrough is insulated from the casing;
 c) a second anode electrically connected to a second feedthrough extending outside the casing, wherein the second feedthrough is insulated from the casing and wherein the feedthroughs for the first and second anodes are spaced apart from each other but isolated from the casing by a single glass-to-metal seal;
 d) a cathode of a cathode active material facing at least a portion of each of the first and second anodes; and
 e) an electrolyte operatively associating the cathode active material with the first and second anodes housed inside the casing.

25. A capacitor, which comprises:
 a) a casing comprising first and second portions, the first portion having a first face wall extending to a surrounding first sidewall and the second portion having a second face wall extending to a surrounding second sidewall, wherein the first and second sidewalls are secured together to provide the casing;
 b) a first anode electrically connected to a first feedthrough extending outside the casing, wherein the first feedthrough is insulated from the casing;
 c) a second anode electrically connected to a second feedthrough extending outside the casing, wherein the second feedthrough is insulated from the casing;
 d) a cathode current collector disposed intermediate the first and second anodes, the cathode current collector having opposed first and second major faces provided with cathode active material facing at least a portion of each of the first and second anodes: and
 e) an electrolyte operatively associating the cathode active material with the first and second anodes housed inside the casing.

26. A capacitor, which comprises:
 a) a casing;
 b) a first anode comprising tantalum and electrically connected to a first feedthrough extending outside the casing, wherein the first feedthrough is insulated from the casing;
 c) a second anode comprising tantalum and electrically connected to a second feedthrough extending outside the casing, wherein the second feedthrough is insulated from the casing;
 d) a cathode of a cathode active material comprising ruthenium and facing at least a portion of each of the first and second anodes; and
 e) an electrolyte operatively associating the cathode active material with the first and second anodes housed inside the casing.

27. The capacitor of claim 26 wherein the first and second face walls support the cathode active material opposite the respective first and second anodes.

* * * * *